(12) United States Patent
Kurokawa et al.

(10) Patent No.: US 6,400,455 B1
(45) Date of Patent: Jun. 4, 2002

(54) OBSERVATION APPARATUS

(75) Inventors: Shuji Kurokawa, Ageo; Kenji Kobayashi, Omiya, both of (JP)

(73) Assignee: Lintec Corporation, Tokyo (JP)

( * ) Notice: Subject to any disclaimer, the term of this patent is extended or adjusted under 35 U.S.C. 154(b) by 0 days.

(21) Appl. No.: 09/209,046

(22) Filed: Dec. 9, 1998

(30) Foreign Application Priority Data

Dec. 18, 1997 (JP) .............................................. 9-364654

(51) Int. Cl.$^7$ .............................................. E01N 21/00
(52) U.S. Cl. .................................................. 356/239.1
(58) Field of Search ........................ 356/237.1, 239.1, 356/239.3

(56) References Cited

U.S. PATENT DOCUMENTS

| | | | | |
|---|---|---|---|---|
| 5,519,496 A | * | 5/1996 | Borgert et al. | 356/394 |
| 5,715,050 A | * | 2/1998 | Haga | 356/237 |
| 5,774,212 A | * | 6/1998 | Corby, Jr. | 356/237 |

FOREIGN PATENT DOCUMENTS

JP    HEI-8-327554    12/1996

* cited by examiner

*Primary Examiner*—Frank G. Font
*Assistant Examiner*—Michael P. Stafira
(74) *Attorney, Agent, or Firm*—Marger Johnson & McCollom, P.C.

(57) ABSTRACT

An observation apparatus for observing an observation object is constructed from a light source portion for emitting illumination light, a converging lens for focusing illumination light from the light source portion onto the observation object and a light-receiving portion for receiving light reflected from the observation object, wherein the light source portion includes a first arrangement of at least one light-emitting body provided on the optical axis of the converging lens, a second arrangement of at least one light-emitting body provided near the optical axis so as to shine light onto the observation object at an incidence angle which allows the light source image to completely cover the light-receiving portion (bright field illumination), a third arrangement of at least one light-emitting body provided near the optical axis so as to shine light onto the observation object at an incidence angle which allows the light source image to cover a portion of the light-receiving portion, and a fourth arrangement of at least one light-emitting body provided near the optical axis so as to shine light onto the observation object at an incidence angle which prevents the light source image from covering any of the light-receiving portion (dark field illumination), in which the light-emitting bodies are adapted for selective activation.

18 Claims, 15 Drawing Sheets

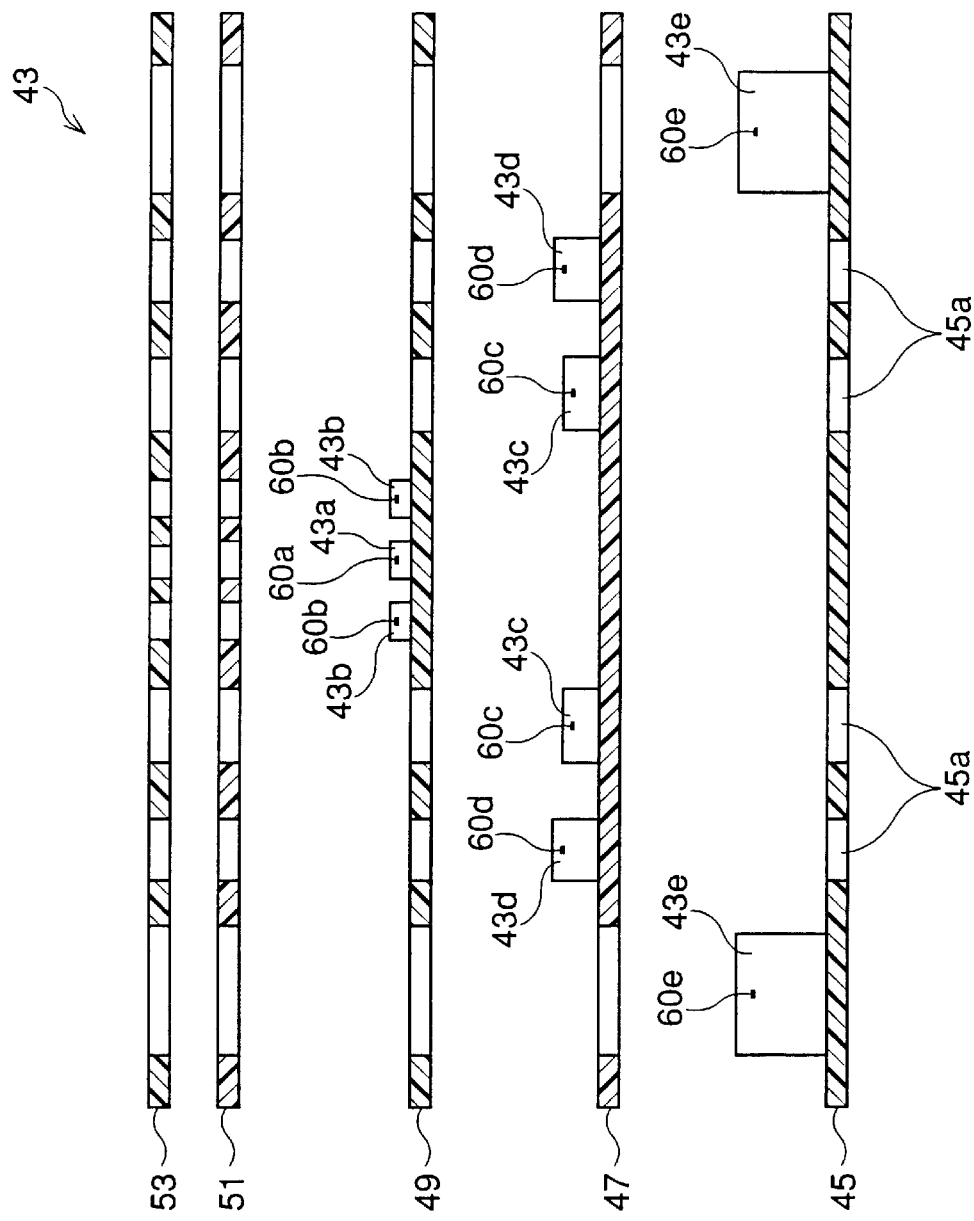

OBSERVATION APPARATUS

BACKGROUND OF THE INVENTION

1. Field of the Invention

The present invention relates to an observation apparatus, and in particular to an observation apparatus for observing patterns such as circuits and characters formed in the surface or near the surface of semiconductor wafers and insulation substrates such as glass, ceramic and the like.

2. Description of the Prior Art

Up to now, during the manufacturing process of semiconductor integrated circuits, observation of patterns such as numbers, characters and circuits provided on the surface of semiconductor wafers (hereinafter referred to simply as "wafer"), liquid crystal substrates, glass, ceramic or resin have been carried out by direct visual inspection or by the use of a camera or microscope. For example, during the manufacturing process, the identification code provided on a wafer are read, and then a predetermined process is carried out in accordance with such identification code.

In observation devices known in the prior art, light source of a fluorescent lamp, fiber optics illumination or a parallel light source through a lens is used to illuminate an observation object in order to perform observation.

In this connection, the present inventor previously proposed (in Japanese Laid-Open Patent Application No. HEI-8-327554) an illumination device for obtaining a high-contrast image, in which light from a light emitting portion is shone by means of an optical element onto an observation object, with the light emitting portion being movable with respect to the optical element in order to make it possible to adjust the illumination angle of the light shining onto the observation object.

SUMMARY OF THE INVENTION

With the invention described above, remarkable results were obtained when the light emission portion was moved to obtain optimum illumination, but it isn't always clear which way the light emission portion should be moved to obtain optimum illumination. Thus, it is an object of the present invention to provide a light source arrangement which makes it easy to obtain an optimum illumination.

In this connection, FIG. 1 shows the principle of the observation apparatus according to the present invention for overcoming the problems described above. As shown in this drawing, the observation apparatus shines light from a light source through an optical element (converging lens 11) and onto an observation object 3a, and a light source portion 13 is equipped with a first light-emitting body 13a, second light-emitting bodies 13b, third light-emitting bodies 13c and 13d and fourth light-emitting bodies 13e, and all these light-emitting bodies are arranged at or near the optical axis 11b of the converging lens 11 within a light source plane 110a arranged at or near the front focal position of the converging lens 11. Further, the light-emitting bodies 13a~13e are selectively activated to illuminate the observation object 3a, and the light reflected from or passing through the observation object is received by a light-receiving portion 7a to be used in observing the observation object 3a.

If the light emitted from any one of the light-emitting bodies strikes the observation object 3a at an incidence angle φ with respect to the optical axis 11b, then the incidence angle φ will become larger as the distance between the light-emitting body and the optical axis 11b increases. In this regard, the incidence angle φ is easily measured based on the focal point distance of the converging lens 11 and the position of the light-emitting body.

The first light-emitting body 13a is arranged on the optical axis 11b, and the second, third and fourth light-emitting bodies are arranged at increasing distances away from the optical axis 11b in that respective order. In this connection, FIG. 2 is a series of drawings showing the relationship between light source images 14a~14e of each of the light-emitting bodies and the light-receiver portion 7a and the image of the observation object 3a formed on the light-receiver portion 7a. Namely, the light source images 14a, 14b, 14c, 14d and 14e correspond respectively to the light source images of the light-emitting bodies 13a, 13b, 13c, 13d and 13e. In this regard, each of the light-emitting bodies carries out the following illumination.

(1) In general, in bright field illumination, if the observation object 3a and the observation plane were a plane mirror, the light from the light-emitting body arranged on the optical axis of the converging lens would reflect off such plane mirror and pass through an image-forming lens 17 at the light-receiving side along a direction aligned with the optical axis of the image-forming lens 17, whereby the light source image will illuminate the entire surface of the light-receiving portion. In the present invention, the first light-emitting body 13a carries out this type of illumination, and the light source image at such time is like that shown in FIG. 2A. Now, in the case where this type of illumination is to be used for characters formed in a wafer by laser etching or the like, if there is no image noise, such characters will generally be observed as dark forms in the shining light source image. However, if there are slight irregularities on the wafer or resist, it is possible for such irregularities to be observed as dark lines (image noise).

(2) By moving the light source to a position slightly away from the optical axis without changing the state in which the light source image covers the entire surface of the light-receiving portion, the present inventor discovered that it is possible to eliminate the dark lines (image noise) due to the above-mentioned irregularities. In the present invention, the second light-emitting bodies 13b carry out this type of illumination, with a light source image being formed as shown in FIG. 2B. In this way, there is also a bright field illumination state in which the light source is positioned slightly away from the optical axis, and it was confirmed that this type of illumination makes it possible to eliminate image noise. The incidence angle φ of this illumination depends on many conditions of the optical system, but a value around φ=20° serves as a good example.

(3) The third light-emitting bodies 13c and 13d are positioned farther away from the optical axis than the light-emitting bodies 13b, with the light-emitting bodies 13d being positioned farther away from the optical axis than the light-emitting bodies 13c, and the incidence angles of the light emitted from the light-emitting bodies 13c and 13d cause their respective light source images 14c and 14d to cover only a partial portion of the light-receiving portion 7a, as shown in FIGS. 2C and 2D. As for the difference between the illumination of the light-emitting bodies 13c and the light-emitting bodies 13d, it should be noted that illumination by the light-emitting bodies 13c involves light from the light source striking the observation object 3a (hereinafter referred to as "incomplete bright field illumination"; see FIG. 2C), and illumination by the light-emitting bodies 13d involves light from the light source not striking the observation object 3a (hereinafter referred to as "incomplete dark field illumination"; see FIG. 2D). In this connection, either of these types of illumination were not used in the prior art because they were considered as incomplete illumination. However, the present inventor confirmed that even with these types of incomplete illumination, it is possible to obtain optimum contrast depending on the properties of the observation object and the incidence angle from the light source. The incidence angle φ of these types of illumination depend on many conditions of the optical system, but a value around φ=5° serves as a good example for the case of incomplete bright field illumination (light-emitting bodies 13c), and a value around φ=7° serves as a good example for the case of incomplete dark field illumination (light-emitting bodies 13d).

(4) The fourth light-emitting bodies 13e are positioned farther away from the optical axis than the light-emitting bodies 13d, and because the light source image 14e doesn't cover any of the light-receiving portion 7a (see FIG. 2E), the fourth light-emitting bodies 13e carry out a dark field illumination. With this type of illumination, the background is dark and the character or pattern portion appears bright. The incidence angle φ of this type of illumination also depends on many conditions of the optical system, but a value around φ=10° serves as a good example.

Further, by selectively activating specific light-emitting bodies among the plurality of light-emitting bodies described above, it is possible to obtain an excellent high-contrast image.

In the present invention, all the light-emitting bodies from the plurality of light-emitting bodies may be used, or only the first, second and fourth arrangement of light-emitting bodies may be used. Furthermore, it is possible to use only the first, third and fourth light-emitting bodies or only the third light-emitting bodies. Further, even thought the third arrangement of at least one light-emitting body is described as having the two sets of light-emitting bodies 13c and 13d, it is possible to provide the third arrangement with only a single set of light-emitting bodies.

As described above, by specifying the light source arrangement, it becomes possible to reliably determine the optimum light source position, and this makes it possible to easily obtain an excellent high-contrast image.

BRIEF DESCRIPTION OF THE DRAWINGS

FIG. 7 is an exploded view of another example of a light source portion.

DETAILED DESCRIPTION OF THE PREFERRED EMBODIMENTS

Figure 1:
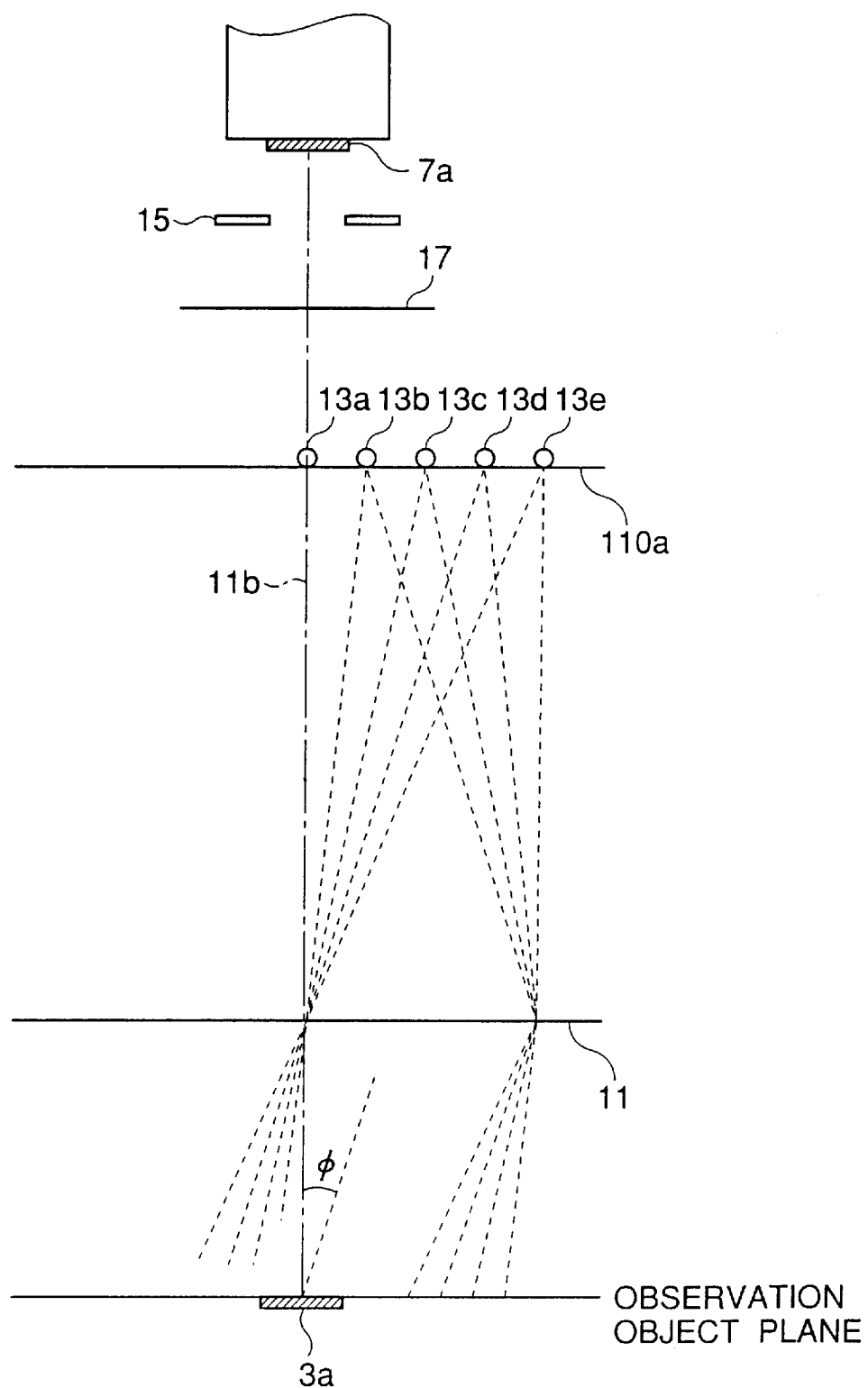
FIG. 1 is an explanatory drawing showing the principle of the observation apparatus of the present invention.
Figure 2A:
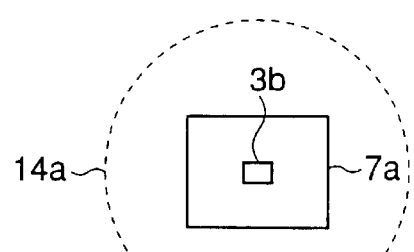
FIGS. 2A to 2E are series of drawings showing the light source images of the first through fourth light-emitting bodies.
Figure 2B:
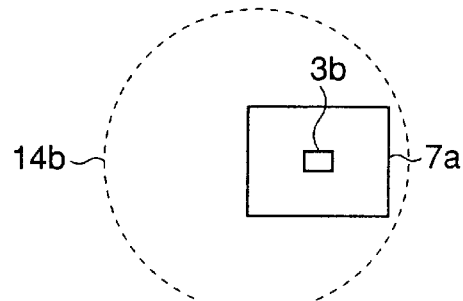
Figure 2C:
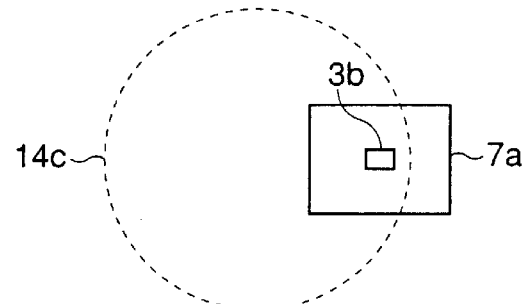
Figure 2D:
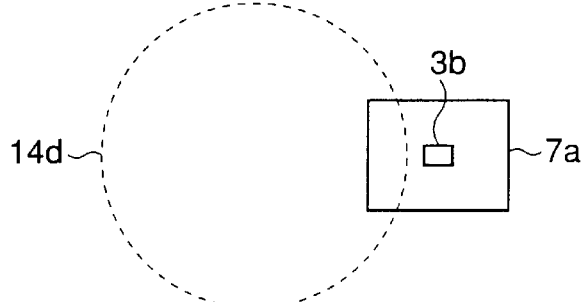
Figure 2E:
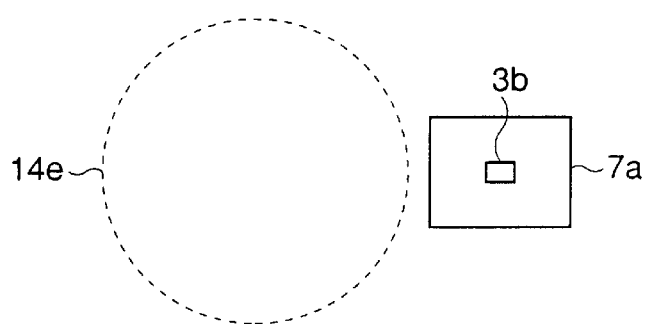
Figure 3:
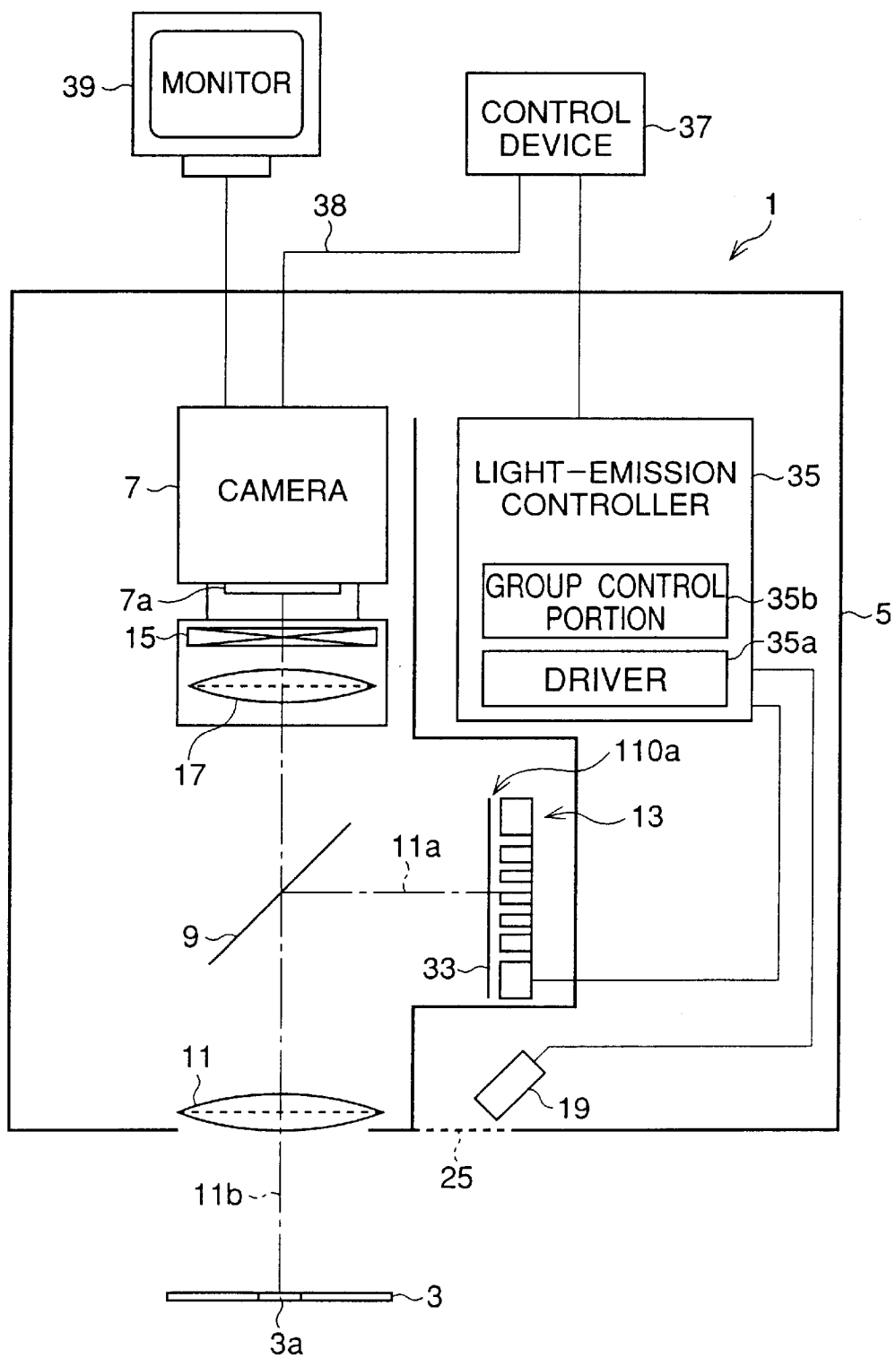
FIG. 3 is a block diagram showing the structure of the observation apparatus.

As shown in FIG. 3, an observation apparatus 1 is used to observe an observation object 3a such as characters or patterns formed in a wafer 3. Each of the structural elements of the observation apparatus 1 are housed in a box 5, and a CCD camera 7 as image detection means, a half mirror 9 and converging lens 11 are arranged from the top of the box 5 to the bottom. At this point, it should be noted that the converging lens 11 functions both as a lens for converging light emitted from a light source portion 13 and as an objective lens arranged between the observation object 3a and a light-receiving portion 7a when forming an image of the observation object 3a onto the light-receiving portion 7a. The light source portion 13 is arranged at the front focal point position of the converging lens 11, and light from the light source portion 13 is reflected downward by the half mirror 9 and converged by the converging lens 11 to shine onto the observation object 3a. Further, the converging lens 11 has an optical axis 11b which passes through the half mirror 9, and an optical axis 11a which is reflected by the half mirror 9.

Figure 5:
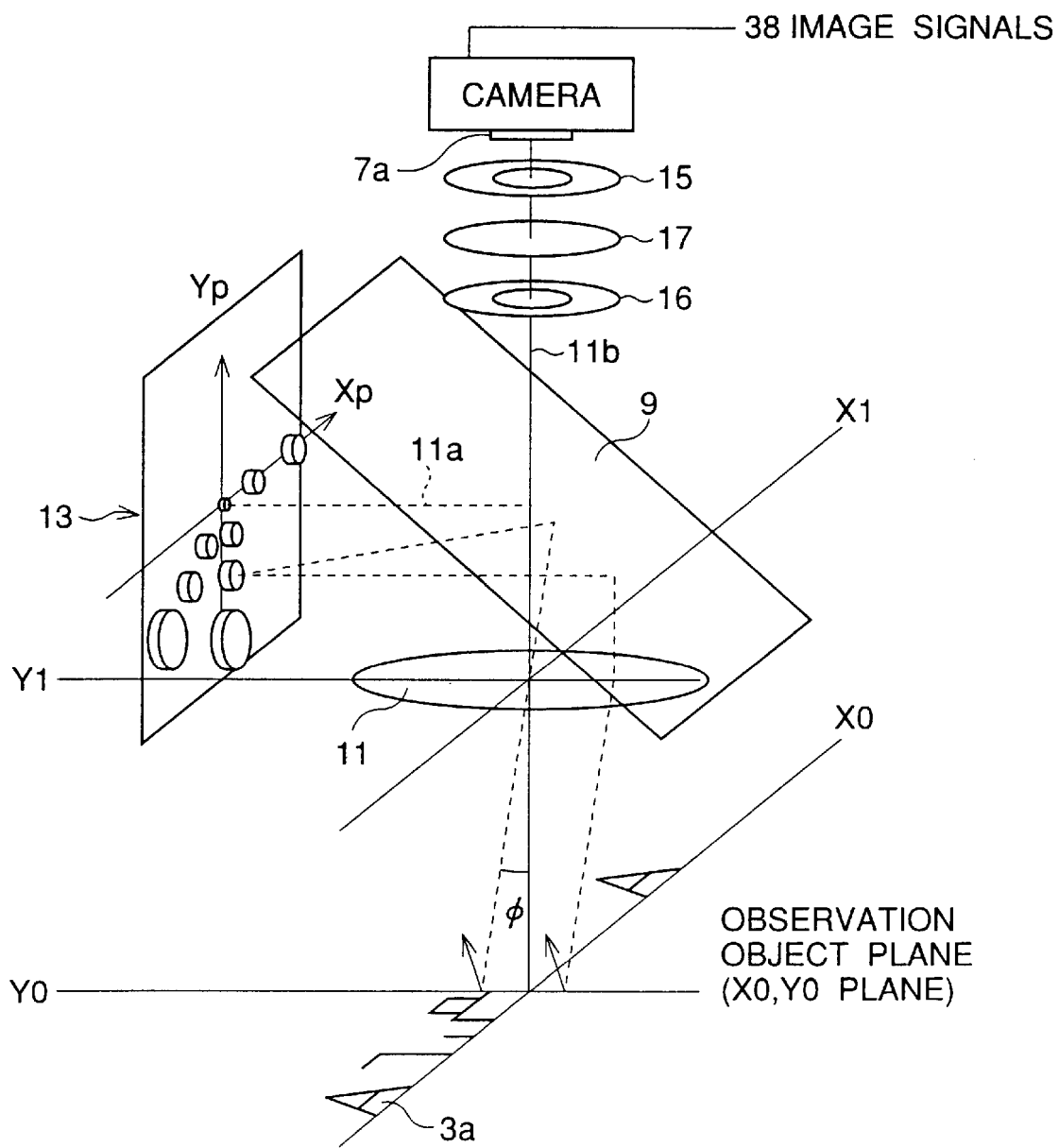
FIG. 5 is a drawing showing the main optical system of the observation apparatus.

The camera 7 is equipped with a diaphragm 15 and an image-forming lens 17, and reflected light from the observation object 3a passes through the half mirror 9, the image-forming lens 17 and the diaphragm 15 in this order, and forms an image on the light-receiving portion 7a (such as a CCD element) of the camera. Further, another diaphragm (the diaphragm 16 shown in FIG. 5) may be provided between the image-forming lens 17 and the half mirror 9.

Figure 4:
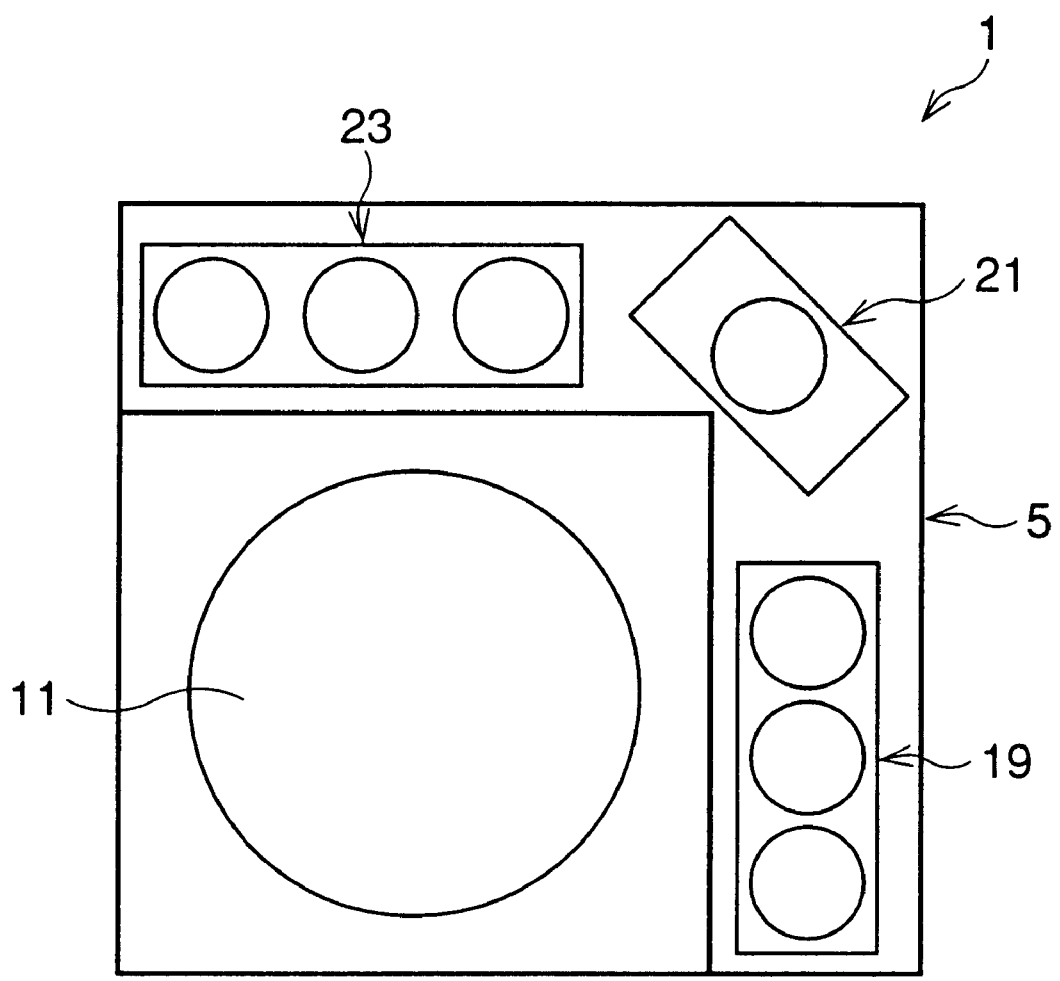
FIG. 4 is a bottom view of the observation apparatus.

As shown in FIG. 4, light-emitting bodies 19, 21 and 23 (which form the fifth arrangement of light-emitting bodies with respect to the first through fourth arrangements described below) are arranged around the converging lens 11 and face toward the observation object 3a, in which the light-emitting bodies 19 and 23 are each formed from three light-emitting elements (such as LEDs), with the light-emitting body 21 being formed from one light-emitting element. The direction in which the light-emitting elements face is set so as to make the light from each of the light-emitting bodies shine onto the observation object 3a. Further, the light from each of the light-emitting bodies may shine onto the observation object 3a directly or through a diffuser 25 (see FIG. 3). This fifth arrangement of light-emitting bodies are used in dark field illumination when carrying out illumination at a large incidence angle (e.g., φ≧11°) so as to be impossible to pass through the converging lens 11.

Figure 6A:
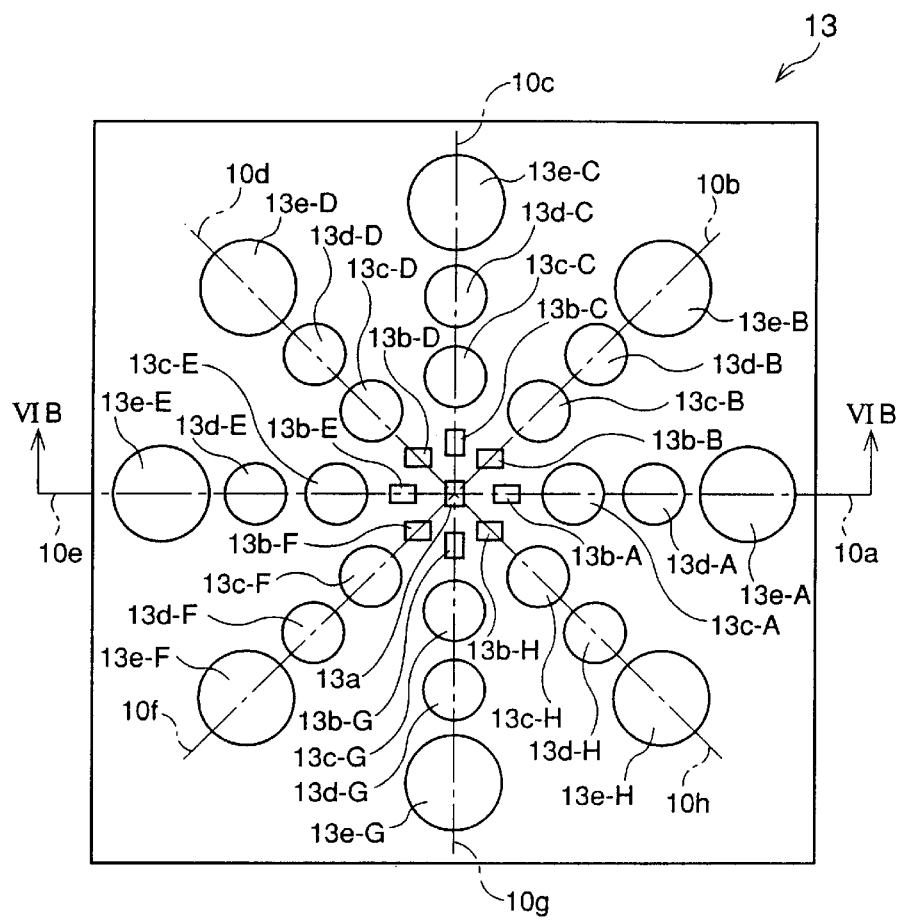
FIGS. 6A and 6B are detailed views of the light source portion.
Figure 6B:
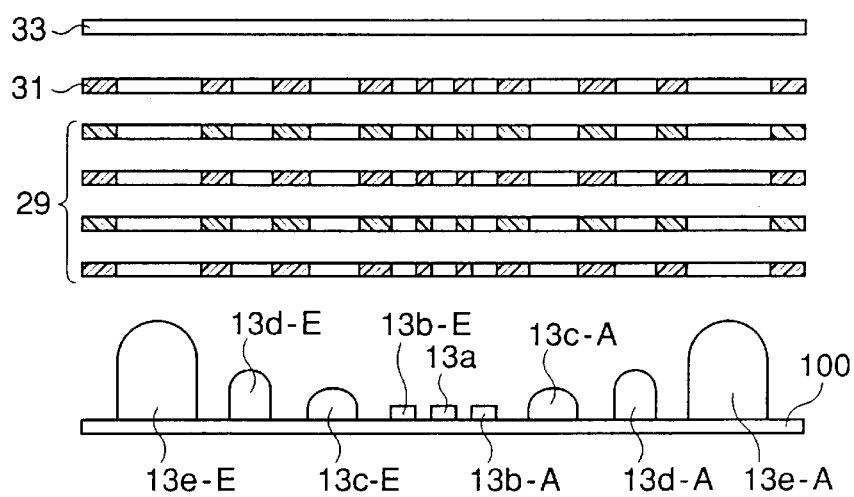

Next, FIGS. 6A and 6B respectively show a side view and a cross-sectional exploded view of the structure of the light source portion 13. As shown in these drawings, the light source portion 13 is equipped with a first light-emitting body 13a arranged at the focal point position of the converging lens 11 on the optical axis 11a, a second light-emitting body 13b arranged in the vicinity of the optical axis 11a to shine light toward the observation object 3a at an incidence angle which makes it possible for the image of the light source to cover the entire surface of the light-receiving portion 7a, third light-emitting bodies 13c, 13d arranged in the vicinity of the optical axis 11a to shine light toward the observation object 3a at an incidence angle which makes it possible for the image of the light source to cover a partial portion of the light-receiving portion 7a, and a fourth light-emitting body 13e arranged in the vicinity of the optical axis 11a to shine light toward the observation object 3a at an incidence angle which makes it possible to avoid the image of the light source from covering the light-receiving portion 7a. Further, the light-emitting body 13a includes one light-emitting element positioned in the center of the light source portion 13, and the second light-emitting body 13b includes 8 light-emitting elements (shown in the drawings as 13b-A, 13b-B, 13b-C, 13b-D, 13b-E, 13b-F, 13b-G and 13b-H) arranged at 45° angular spacings around the center-located first light-emitting body 13a. Similarly, each of the third light-emitting bodies 13c, 13d includes eight light-emitting elements arranged at 45° angular spacings around the second light-emitting body 13b, and the fourth light-emitting body 13e includes eight light-emitting elements arranged at 45° angular spacings around the third light-emitting bodies 13c, 13d.

The power of the light-emitting bodies increases as the position moves outward from the center. Namely, the power of the light-emitting bodies increases with increasing distance from the optical axis 11a, and in this way it becomes possible to prevent weakening of the light which illuminates the observation object 3a. Further, because the illumination surface area increases and the reflected light from the observation object becomes weaker as the incidence angle increases, it is necessary to make the light emission intensity of the light source stronger with increasing distance from the optical axis, as described above. In this connection, even though the light-emitting bodies are shown in FIG. 6 as increasing in size with increasing distance from the center, the present embodiment is not limited to this structure, and it is only necessary for the light-emitting bodies to have stronger emission intensities with increasing distance from the center.

The light-emitting bodies shown in FIG. 6 are LEDs, and in general an LED has some directional characteristics at around 90° or near with respect to its optical axis (i.e., the 0° direction). Further, the tips of the light-emitting bodies 13c~13e are formed from resin so as to have a hemispherical projectile shape in order to obtain a sharp peak near its 0° direction. Further, because the light-emitting bodies 13a, 13b are arranged as close as possible to the optical axis 11a, compact chip LEDs are used.

As shown in FIG. 6B, each of the light-emitting bodies is provided on a circuit substrate 100, above which a plurality of light-blocking plates 29, a diaphragm plate 31 and a diffuser 33 are stacked in that order and fixed in place by screws or the like. Further, holes which enable the light-emitting bodies to pass therethrough are formed in the light-blocking plates 29 at positions corresponding to the light-emitting bodies, and by passing the light-emitting bodies through these holes, the light-blocking plates 29 are stacked thereon. Now, by blocking off light between adjacent light-emitting bodies, the light-blocking plates 29 prevent the occurrence of false emission caused by 90° directional light intruding into neighboring light-emitting bodies which are not in a light-emitting state. In this regard, the number of plates used for the light-blocking plates 29 is determined in accordance with the height of the light-emitting bodies. Further, holes which are the same or slightly smaller than the holes in the light-blocking plates 29 are formed in the diaphragm plate 31 at positions corresponding to the light-emitting bodies, and by controlling the size of these holes, it is possible to adjust the amount of light directed toward the diffuser 33. Further, the position of the diffuser 33 forms the position of a light source surface 110a with respect to the converging lens 11.

The diffuser 33 in FIG. 6B is shown as covering whole holes of the diaphragm plate 31 and light-blocking plates 29, but in case where the emission intensity of specific light-emitting bodies are to be given precedence, the holes of such light-emitting bodies are not covered. However, this case requires caution due to the fact that the lens effect of the tip shape of the light-emitting bodies can cause the emission positions of such uncovered light-emitting bodies to be different from what they would be in the case where they are covered by the diffuser 33.

Next, FIG. 7 gives a view of an example structure in which the diffuser used in FIG. 6 is omitted. In this structure, the tip of each of the LEDs is formed into a flat surface instead of a projectile shape. In this way, the peak around the 0° direction disappears and the light-emitting bodies exhibit directional characteristics over a wider angle, and this allows the light from the light-emitting bodies to enter through the entire surface of the converging lens, whereby the light-emitting bodies appear roughly as a point light source for the converging lens. Further, in the case where the height of the light-emitting bodies (LEDs) are different from each other in this example, the structure is arranged so that the light-emitting positions 60a~60e of the light-emitting bodies are positioned in the same plane. Namely, the light source portion 43 is constructed from a substrate 45 mounted with the tallest light-emitting bodies 43e, a substrate 47 mounted with intermediate height light-emitting bodies 43c and 43d, a substrate 49 mounted with the shortest light-emitting bodies 43a and 43b, a light-blocking plate 51 and a diaphragm plate 53 stacked in that order. Further, through-holes 45a are formed in the substrate 45 to enable the lead wires of the light-emitting bodies 43c and 43d mounted on the substrate 47 to pass through the substrate 45. Similarly, holes are formed in the diaphragm plate, light-blocking plate and each of the substrates at positions corresponding to positions of the light-emitting bodies, and by passing the light-emitting bodies through such holes, it is possible to stack all these elements together. In this way, the plane formed at the light emission positions 60a~60e of the light-emitting bodies forms the light source surface 110a, and by aligning this light source surface 110a with the focal plane of the converging lens 11, the light from the light-emitting bodies roughly forms a point light source which makes it possible to illuminate the observation object 3a with parallel rays of light.

The light-emitting bodies 13a~13e are arranged along lines 10a~10h (see FIG. 6A) which intersect the optical axis 11a in the light source surface 110a arranged at or near the front focal point position of the converging lens 11. Now, by arranging the light-emitting bodies on lines which intersect the optical axis, only light-emitting bodies effective for observation are arranged, and this makes it possible to eliminate ineffectiveness. Consequently, this makes it possible to reduce the size of the drive circuit for the light-emitting bodies, and light emission control becomes relatively easy. A description directed to these points will now be given below.

Figure 8:
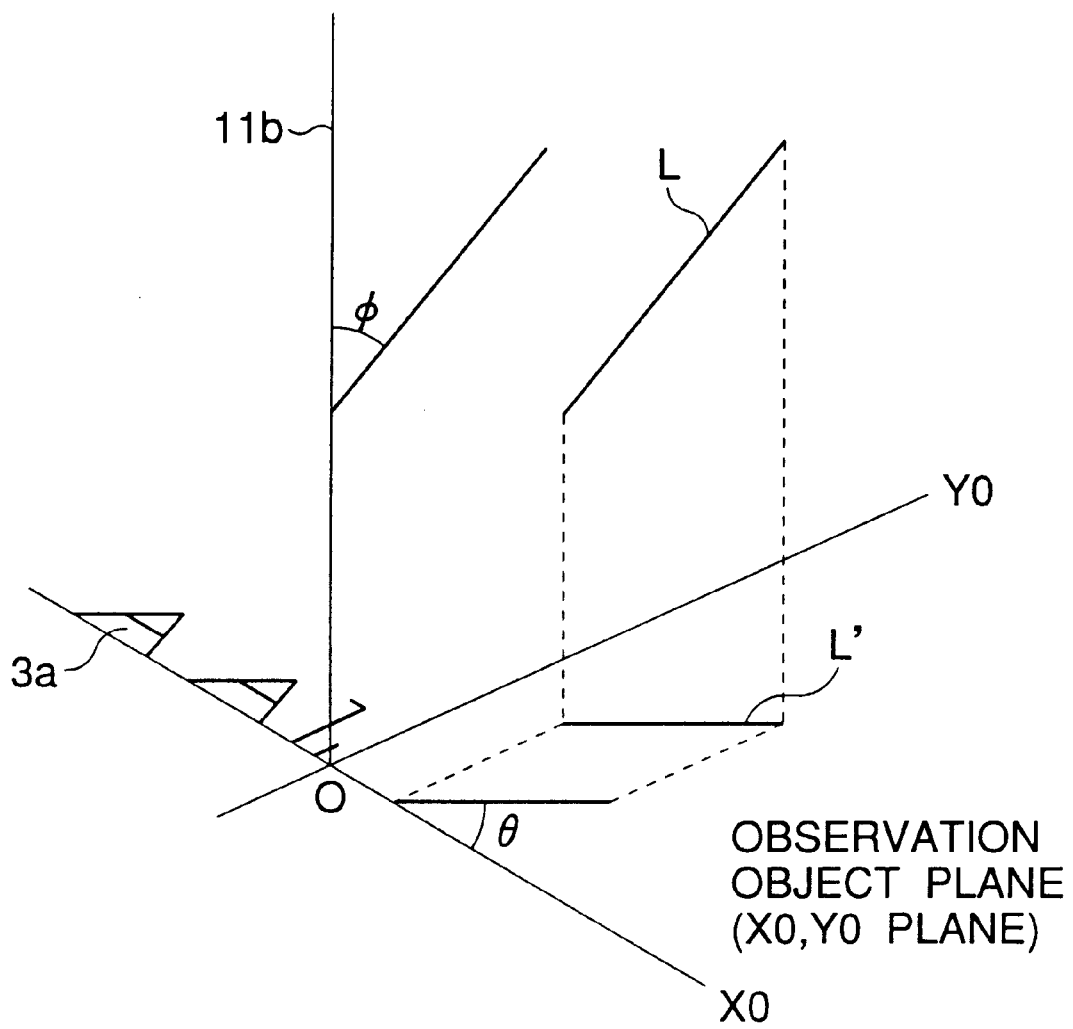
FIG. 8 is a drawing explaining the angle θ.

First, it should be noted that adjacent lines of the lines 10a~10h intersect each other at an angle of 45°. The meaning of this angular intersection will be explained with reference to FIG. 8. Namely, in the coordinate arrangement shown in FIG. 8, the configuration direction of the observation object 3a forms the reference direction, the point of intersection between the optical axis 11b of the optical system and the plane of the observation object 3a forms the origin O, the line which extends out from the origin O along the reference direction forms a X0 axis, and the line which extends out from the origin O along a direction orthogonal to the X0 axis forms a Y0 axis. Further, the light rays incident on the observation object 3a are represented by a vector L which forms a projection L' onto the plane containing the observation object 3a (i.e., the X0-Y0 plane), with θ representing the angle between the projection L' and the X0 axis. Namely, the angle θ represents the angle of the incident light rays L with respect to the configuration direction of the observation object 3a. The value of this angle θ is extremely important in carrying out observations with the proper contrast.

Returning to FIG. 6 for further description, the line 10a is aligned with the reference direction of the observation object 3a, and the angle θ of the illumination light from the light-emitting bodies on line 10a is 0°. Namely, the light-emitting bodies 13b-A, 13c-A, 13d-A and 13e-A are all at θ=0°. Further, the angle θ of each of the lines 10b~10h and a listing of their respective light-emitting bodies arranged on the lines is given below:

| Line 10b: | θ = 45° | 13b-B, 13c-B, 13d-B and 13e-B |
| Line 10c: | θ = 90° | 13b-C, 13c-C, 13d-C and 13e-C |
| Line 10d: | θ = 135° | 13b-D, 13c-D, 13d-D and 13e-D |
| Line 10e: | θ = 180° | 13b-E, 13c-E, 13d-E and 13e-E |
| Line 10f: | θ = 225° | 13b-F, 13c-F, 13d-F and 13e-F |
| Line 10g: | θ = 270° | 13b-G, 13c-G, 13d-G and 13e-G |
| Line 10h: | θ = 315° | 13b-H, 13c-H, 13d-H and 13e-H |

It should be noted that the angle θ is not limited to 45° and whole number multiples thereof, and it is possible to use other angles. Further, the optimum angle θ value varies depending on the properties of the observation object. For example, when observing circuit patterns are formed in wafers, there are many cases where the configuration direction of the circuit elements and the running direction of the wiring pattern are orthogonal each other. In such cases, there is a tendency that strong light shining from the circuit pattern is observed at θ=0°, 90°, 180° and 270°, and no light shining from the circuit pattern is observed at θ=45°, 135°, 225° and 315°. In this connection, in the case where characters are arranged on the circuit pattern to serve as the observation object 3a, setting the angle at θ=45° and whole number multiples thereof makes it easy to observe the observation pattern 3a without light shining from the background circuit pattern.

Further, in the case where characters are formed on the wafer by a plurality of thin-grooved 45° angle slanting lines, setting the angle only at θ=45° or 225° and at θ=135° or 315° is effective for observing these types of characters, and in this case, illumination in from the other light sources is ineffective and a potential cause of image noise such as resist noise and the like.

Now, with reference to FIG. 3, the light source portion 13 and the fifth light-emitting bodies 19, 21 and 23 are controlled by a light-emission controller 35. The light-emission controller 35 is constructed with a driver 35a and a group control portion 35b, with the driver 35a being used to control the ON/OFF state and the emission intensity of each of the light-emitting bodies. The group control portion 35b divides the light-emitting bodies that make up the light source portion into groups and specifies the groups of light-emitting bodies that should be used for illumination in accordance with the observation object 3a. This will be described in more detail later. Further, the light-emission controller 35 is controlled by a control device (such as a computer) 37 and is equipped with systems such as an OCR system and pattern inspection system. Further, image signals 38 from the camera 7 are displayed on a monitor 39 and outputted to the control device 37 to undergo image recognition.

Figure 9:
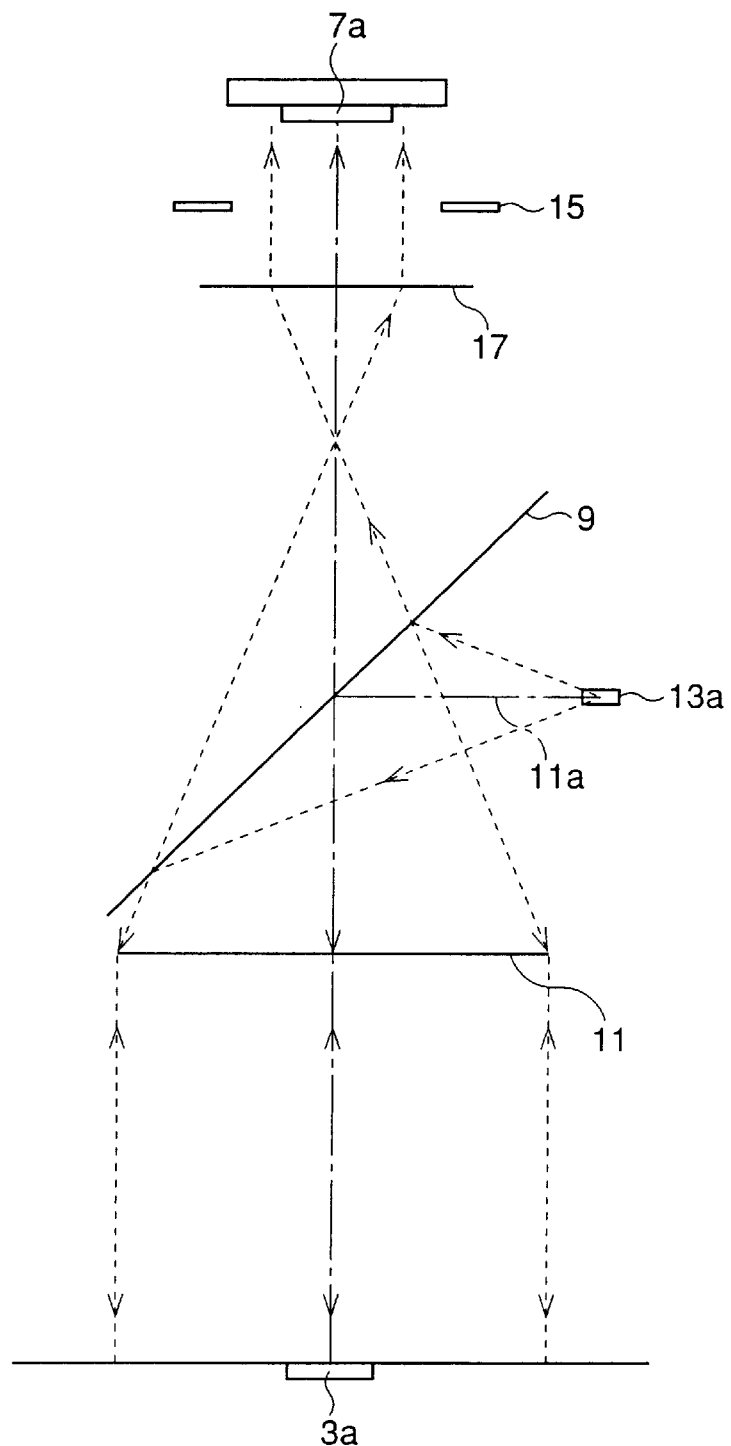
FIG. 9 is a drawing showing the optical path used by the first light-emitting body.
Figure 10:
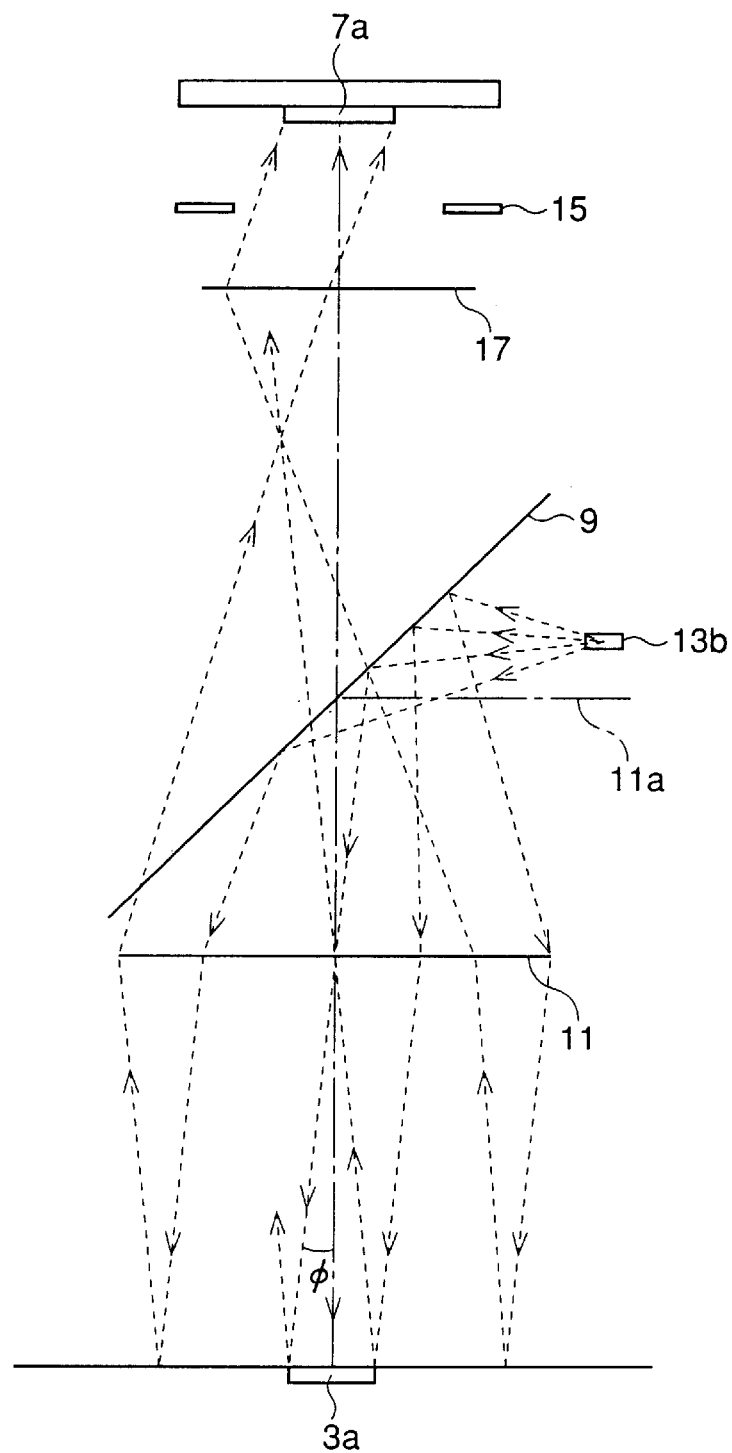
FIG. 10 is a drawing showing the optical path used by the second light-emitting bodies.
Figure 11:
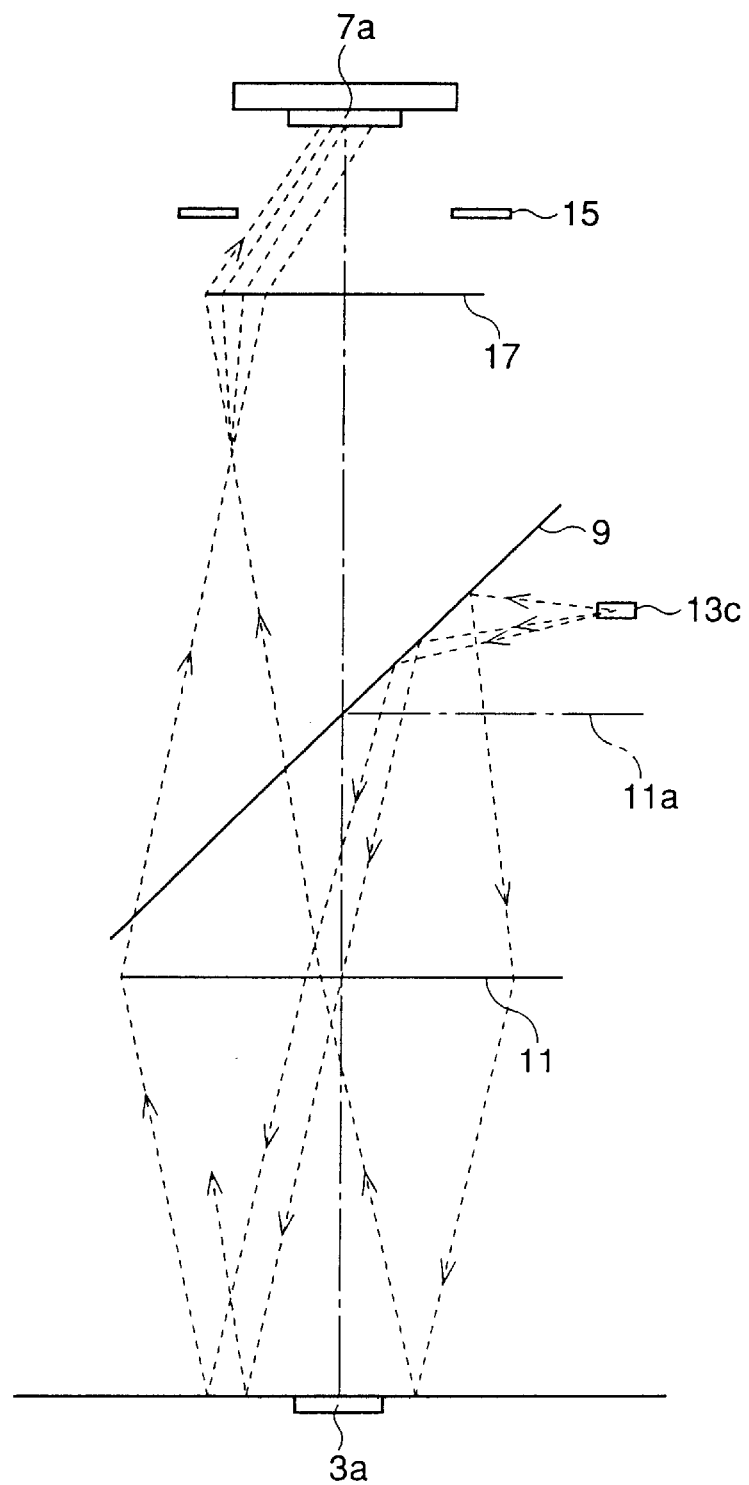
FIG. 11 is a drawing showing the optical path used by the third light-emitting bodies for incomplete bright field illumination.
Figure 12:
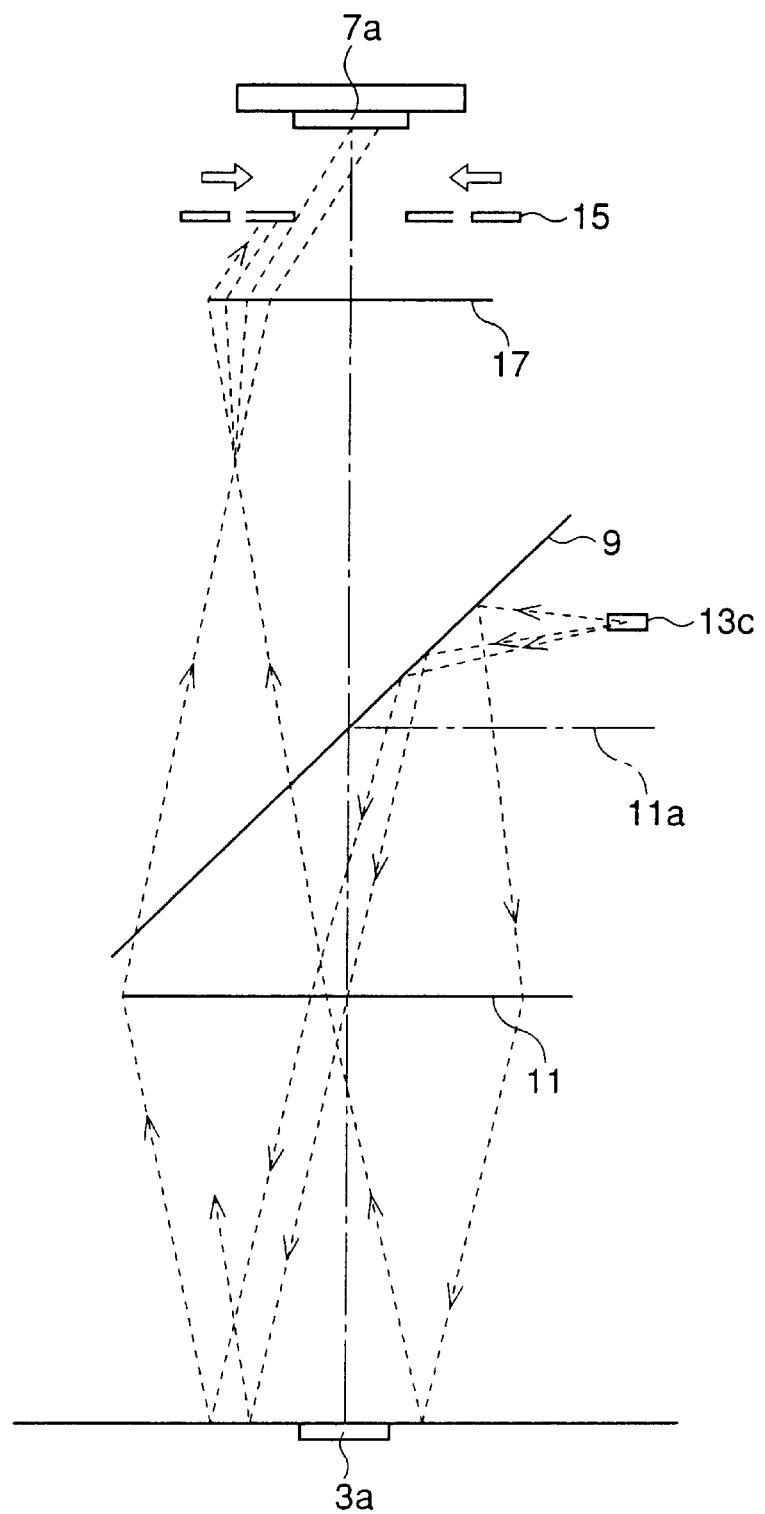
FIG. 12 is an optical path drawing explaining the use of a diaphragm.
Figure 13:
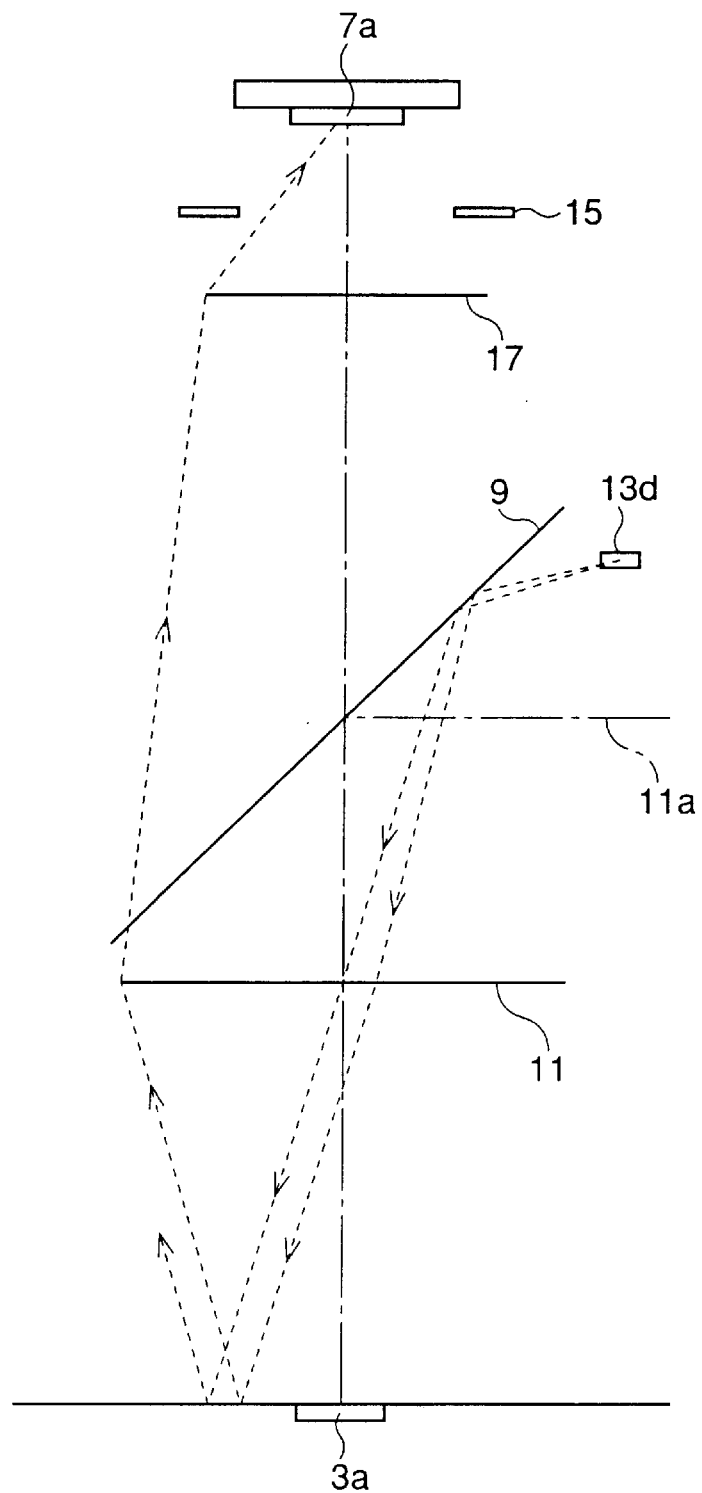
FIG. 13 is a drawing showing the optical path used by the third light-emitting bodies for incomplete dark field illumination.

Next, FIGS. 9~15 show the optical paths for light from each of the light-emitting bodies, and as shown in FIG. 9, the light from the light-emitting body 13a forms a bright field illumination in which the image of the light source covers the entire surface of the light-receiving portion 7a. As shown in FIG. 10, the light from the light-emitting bodies 13b shines onto the observation object 3a at a slight incidence angle φ, and because the image of the light source covers the entire surface of the light-receiving portion 7a, the light-emitting bodies 13b carry out a bright field illumination similar to that of the light-emitting body 13a. As shown in FIG. 11, the light from the light-emitting bodies 13c shines onto the observation object 3a at a little larger incidence angle, and because the image of the light source covers only a portion of the light-receiving portion 7a, the light-emitting bodies 13c carry out an incomplete bright field illumination. At this time, as shown in FIG. 12, if the diaphragm 15 is closed so as to block off a portion of the light incident on the light-receiving portion 7a, it becomes possible to carry out an incomplete dark field illumination. Namely, by opening and closing the diaphragm 15, it is possible to switch between a bright field illumination and a dark field illumination. Further, FIG. 13 shows the incomplete dark field illumination carried out by the light-emitting bodies 13d.

Figure 14:
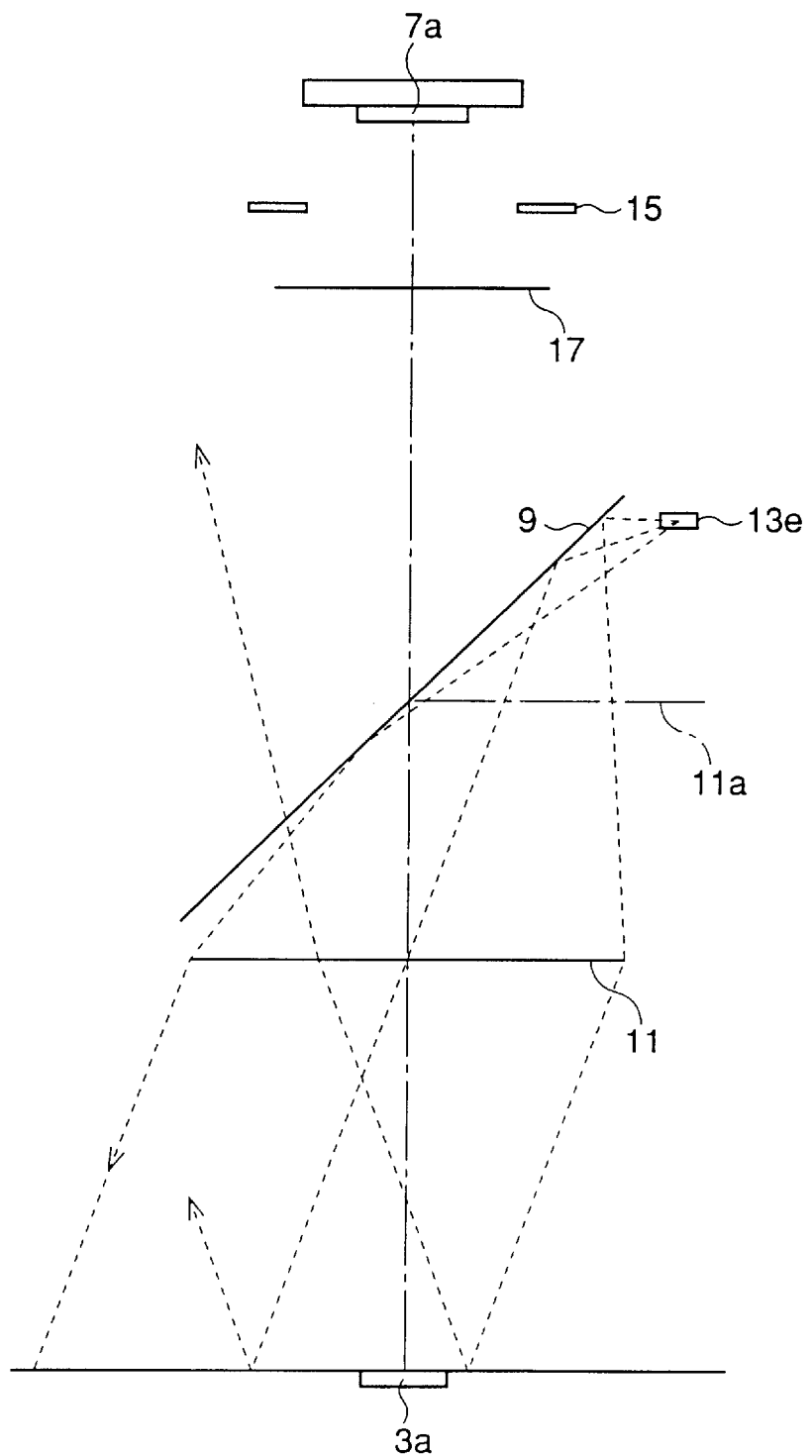
FIG. 14 is a drawing showing the optical path used by the fourth light-emitting bodies.
Figure 15:
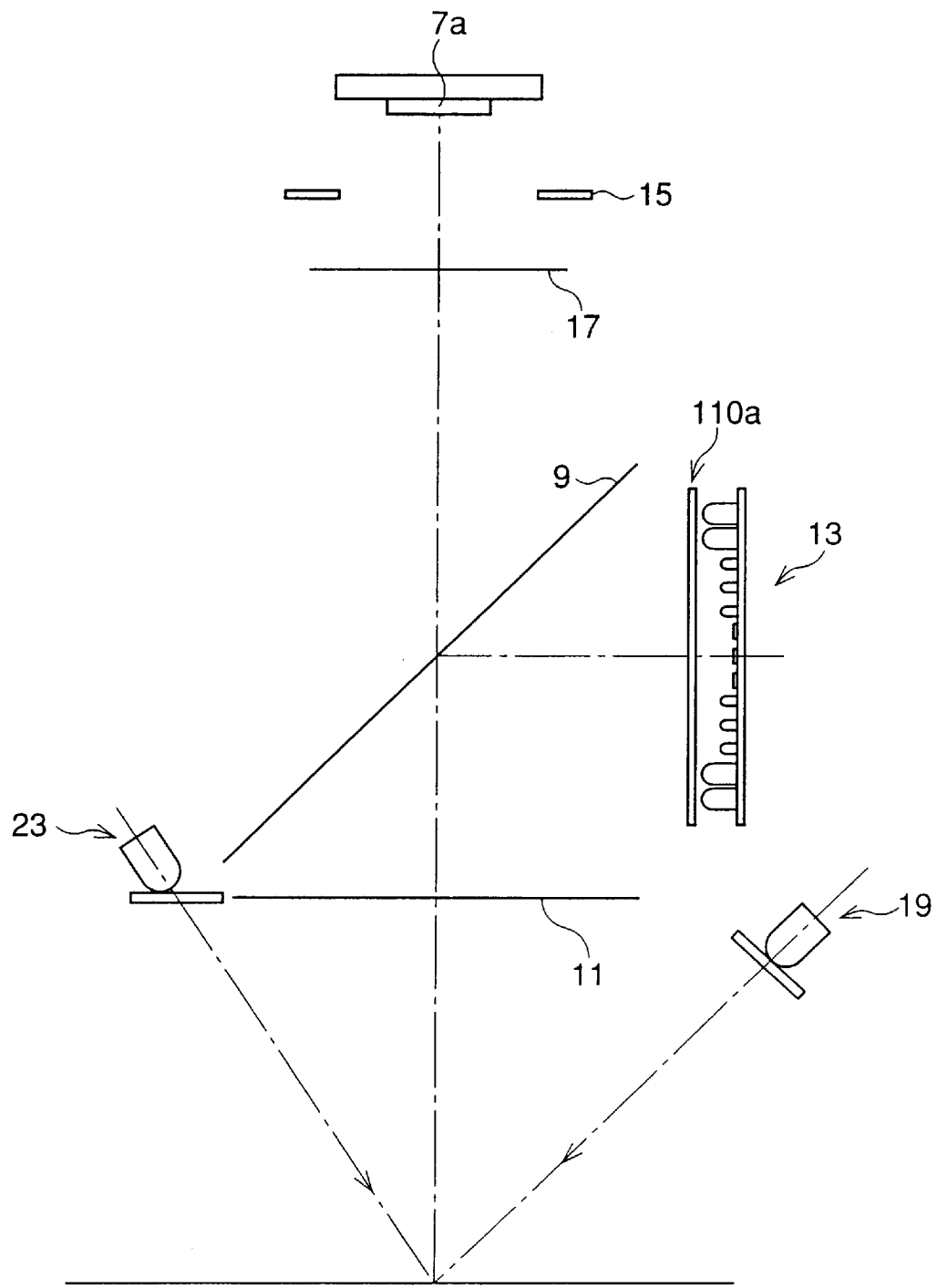
FIG. 15 is a drawing showing the optical path used by the fifth light-emitting bodies.

FIG. 14 shows the dark field illumination carried out by the light-emitting bodies 13e, in which the image of the light source does not cover any of the light-receiving portion 7a. Further, FIG. 15 shows the dark field illumination carried out by the fifth light-emitting bodies 19 and 23. In this connection, as was described above, this illumination is due to a large incidence angle in which no light passes through the converging lens 11.

Next, Table 1 shows a group table stored in the group control portion 35b (shown in FIG. 3), and stored in this table are the names (such as 13c-A shown in FIG. 6) of the light-emitting bodies activated for each group and the emission intensity (shown as index numbers in the table) for each of the light-emitting bodies. This data may be stored in the ROM of the group control portion 35b or inputted from the outside. Thus, upon receiving instructions from the control device 37, the group control portion 35b specifies a particular group name of Table 1 and outputs light emission instructions to the driver 35a. Then, based on such instructions, the driver 35a selects the appropriate light-emitting bodies (i.e., the light-emitting bodies effective in obtaining low-noise, high-contrast observations; and not limited to one selection) and carries out illumination at the designated emission intensities.

TABLE 1

|  | Name of Light-Emitting Bodies | Emission Intensity |
|---|---|---|
| Group A | Light-Emitting Body 13c-A | 100 |
|  | Light-Emitting Body 13d-A | 50 |
|  | Light-Emitting Body 13e-A | 25 |
| Group B | Light-Emitting Body 13c-D | 100 |
|  | Light-Emitting Body 13d-H | 100 |

Next, Table 2 shows another example of a group table, and in this example the emission intensity includes data on the emission range (i.e., the upper limit value and the lower limit value) and the fluctuation value for the fluctuation of the emission intensity of the light-emitting bodies within the emission range, and in accordance with instructions from the group control portion 35b, the emission intensity is varied within the emission intensity range.

TABLE 2

|  | Name of Light-Emitting Bodies | Emission Intensity | [*A] | [*B] | Fluctuation Value |
|---|---|---|---|---|---|
| Group A | Light-Emitting Body 13a | 100 | 60 | 100 | 10 |
|  | Light-Emitting Body 13b-C | 50 | 20 | 60 | 5 |
| Group B | Light-Emitting Body 13c-G | 25 | 0 | 30 | 5 |
|  | Light-Emitting Body 13d-G | 100 | 70 | 100 | 5 |
|  | Light-Emitting Body 13e-C | 100 | 80 | 100 | 15 |

[*A]: Lower Limit Emission Intensity
[*B]: Upper Limit Emission Intensity

The above-describe group emission (i.e., simultaneous light emission with a plurality of light-emitting bodies) is effective in (1) compensating any insufficient light emission intensity, (2) eliminating contrast irregularities of the observation object, and (3) eliminating background noise of the observation object. In this connection, instead of carrying out observations under the same illumination conditions (such as emission intensity), in many cases good observation results can be obtained by changing the conditions. This is believed to be due to the curvature of individual observation objects and variations of optical conditions. Thus, when considering the example of a wafer, by carrying out trial illumination while changing the conditions in accordance with the resist irregularities and the strength of the background pattern noise, it is possible to find good illumination conditions for obtaining good observation results. At such time, if the changes in conditions are restricted to an established range, the number of changes in conditions will be reduced, and this makes it possible to eliminate useless trials. In the case where there is a plurality of groups, by arranging an order of priority for such groups according to the purpose of observation, the group light emission can be carried out in an order from the group with the highest priority.

In the above-described group light emission, the emission conditions of each of the light-emitting bodies included emission intensity, emission intensity range and fluctuation values which were set so as to be variable, but the light emission conditions are not limited to the conditions described above, and it is possible to use other conditions.

Next, an example method of using the above-described observation apparatus will be given below.

When used as a reading apparatus for reading characters and symbols formed in a wafer, the first step involves placing the observation apparatus of the present invention at an appropriate position in the manufacturing process. Next, the wafer is conveyed manually or automatically to a location that positions the observation object 3a directly below the converging lens 11. Then one or more of the light-emitting bodies 13a~13e are driven to illuminate the observation object 3a, and in this illumination state, the camera 7 picks up images to enable the control device 37 to read such characters and symbols. In this connection, the light-emitting bodies that will be driven are established in advance in the light-emission controller 35. Now, if an error occurs in the reading result, the light-emitting bodies are changed or new light-emitting bodies are added, and then the steps of illumination and reading are repeated.

The light-emitting bodies to be used for illumination can be determined in advance based on data. For example, a test can be carried out in advance to select the light-emitting bodies capable of achieving a high contrast from the light-emitting bodies 13a~13e. In this regard, a single or plural arrangement of light-emitting bodies (i.e., a combination of light sources according to the incidence angle $\phi$ and the angle $\theta$) capable of producing optimum illumination are stored in advance as data inputted into the light-emission controller 35 from the outside. Further, by arranging an order of priority for such data, operations can be carried out in an order starting from the illumination with the highest priority. Of course, it is also possible to carry out a group light emission as described above.

In the observation apparatus described above, the use of a half mirror 9 to form a branching optical path onto which the light source is arranged makes it possible for the converging lens 11 to function both as a converging lens and an objective lens. However, the present invention is not limited to this structure, and it is possible to eliminate the half mirror and use separate objective and converging lenses. However, the use of the half mirror 9 is preferred because the ability of the converging lens 11 to function both as a converging lens and an objective lens makes it possible to construct a compact observation apparatus. Further, the observation apparatus according to the present invention is not limited to the above-described optical system in which observation is carried out using light reflected from the observation object, and it is possible provide the observation apparatus with an optical system in which the light emitted from the light-emitting bodies is adapted to pass through the observation object, with observation of the observation object being carried out using the light that passes through the observation object.

When the light source surface is moved away from the focal point position, the illumination converges and diverges with respect to the observation object, and depending on the observation object, there are cases where this makes it possible to obtain a high-contrast image. In such cases, the light source is arranged at a position away from the focal point position to make it possible to obtain an optimum image. In other words, depending on the observation object, the light source is arranged near the focal plane of the converging lens.

In the embodiment described above, observations were carried out with a CCD sensor placed at the light-receiving portion 7a, but the present invention is not limited to this structure, and it is possible to use other sensors or an image pickup tube, or observations may be carried out with the naked eye.

As described above, because the observation apparatus of the present invention can specify the light source arrangement, it is possible to reliably determine the optimum light source position, and as a result it becomes possible to easily obtain an excellent high-contrast image.

What is claimed is:

1. An observation apparatus for observing an observation object, comprising:

a light source portion equipped with a plurality of light-emitting bodies;

an optical element for focusing illumination light from the light source portion onto the observation object; and a light-receiving portion for receiving light reflected from or passing through the observation object;

wherein the light source portion is arranged at or near the focal plane of the optical element and includes:

a first arrangement of at least one light-emitting body for providing a first bright field illumination, arranged on the optical axis of the optical element;

a second arrangement of at least one light-emitting body for providing a second bright field illumination, arranged near the optical axis so as to shine light onto the observation object at an incidence angle which allows the light source image to completely cover the light-receiving portion;

a third arrangement of at least one light-emitting body for providing an incomplete bright field or incomplete dark field illumination, arranged near the optical axis so as to shine light onto the observation object at an incidence angle which allows the light source image to cover a partial portion of the light-receiving portion; and a fourth arrangement of at least one light-emitting body for providing a dark field illumination, arranged near the optical axis so as to shine light onto the observation object at an incidence angle which prevents the light source image from covering any of the light-receiving portion, in which the light-emitting bodies are adapted for selective activation.

2. An observation apparatus for observing an observation object, comprising:

a light source portion equipped with a plurality of light-emitting bodies;

an optical element for focusing illumination light from the light source portion onto the observation object; and a light-receiving portion for receiving light reflected from or passing through the observation object;

wherein the light source portion is arranged at or near the focal plane of the optical element and includes:

a first arrangement of at least one light-emitting body for providing a first bright field illumination, arranged on the optical axis of the optical element;

a second arrangement of at least one light-emitting body for providing a second bright field illumination, arranged near the optical axis so as to shine light onto the observation object at an incidence angle which allows the light source image to completely cover the light-receiving portion; and a fourth arrangement of at least one light-emitting body for providing a dark field illumination, arranged near the optical axis so as to shine light onto the observation object at an incidence angle which prevents the light source image from covering any of the light-receiving portion, in which the light-emitting bodies are adapted for selective activation.

3. An observation apparatus for observing an observation object, comprising:

a light source portion equipped with a plurality of light-emitting bodies;

an optical element for focusing illumination light from the light source portion onto the observation object; and a light-receiving portion for receiving light reflected from or passing through the observation object;

wherein the light source portion is arranged at or near the focal plane of the optical element and includes:

a first arrangement of at least one light-emitting body for providing a first bright field illumination, arranged on the optical axis of the optical element;

a third arrangement of at least one light-emitting body for providing an incomplete bright field or incomplete dark field illumination, arranged near the optical axis so as to shine light onto the observation object at an incidence angle which allows the light source image to cover a partial portion of the light-receiving portion; and a fourth arrangement of at least one light-emitting body for providing a dark field illumination, arranged near the optical axis so as to shine light onto the observation object at an incidence angle which prevents the light source image from covering any of the light-receiving portion, in which the light-emitting bodies are adapted for selective activation.

4. An observation apparatus for observing an observation object, comprising:

a light source portion for emitting illumination light;

an optical element for focusing illumination light from the light source portion onto the observation object; and a light-receiving portion for receiving light reflected from or passing through the observation object;

wherein the light source portion is arranged at or near the focal plane of the optical element and includes a third arrangement of at least one light-emitting body for providing an incomplete bright field or incomplete dark field illumination, arranged near the optical axis of the optical element so as to shine light onto the observation object at an incidence angle which allows the light source image to cover a partial portion of the light-receiving portion.

5. The observation apparatus of claim 4, further comprising a diaphragm for restricting the light reflected from or passing through the observation object before such light reaches the light-receiving portion when the third arrangement of at least one light-emitting body is activated, whereby the opening and closing the diaphragm switches the illumination between a bright-field illumination and a dark field illumination.

6. The observation apparatus of claim 4, wherein the third arrangement of at least one light-emitting body comprises a plurality of light-emitting bodies.

7. The observation apparatus of claim 6, wherein the light-emitting bodies are arranged at or near the focal plane of the optical element along lines which intersect the optical axis of the optical element.

8. The observation apparatus of claim 2, wherein the light-emitting bodies are arranged at or near the focal plane of the optical element along lines which intersect the optical axis of the optical element.

9. The observation apparatus of claim 7, wherein the angular spacing between adjacent lines which intersect the optical axis of the optical element is 45°.

10. The observation apparatus of claim 8, wherein the angular spacing between adjacent lines which intersect the optical axis of the optical element is 45°.

11. The observation apparatus of claim 2, wherein the light-emitting bodies are separated into groups which can be activated separately to carry out illumination, each group comprising a plurality of the light-emitting bodies to be activated simultaneously.

12. The observation apparatus of claim 4, wherein the light-emitting bodies are separated into groups which can be activated separately to carry out illumination, each group comprising a plurality of the light-emitting bodies to be activated simultaneously.

13. The observation apparatus of claim 11, wherein a light emission priority order is established for the groups of light-emitting bodies.

14. The observation apparatus of claim 12, wherein a light emission priority order is established for the groups of light-emitting bodies.

15. The observation apparatus of claim 11, wherein the light-emitting bodies in each group have adjustable light emission intensity.

16. The observation apparatus of claim 12, wherein the light-emitting bodies in each group have adjustable light emission intensity.

17. The observation apparatus of claim 2, further comprising a fifth arrangement of at least one light-emitting body for shining light onto the observation object without passing through the optical element.

18. The observation apparatus of claim 4, further comprising a fifth arrangement of at least one light-emitting body for shining light onto the observation object without passing through the optical element.

* * * * *

UNITED STATES PATENT AND TRADEMARK OFFICE
CERTIFICATE OF CORRECTION

PATENT NO.    : 6,400,455 B1
DATED         : June 4, 2002
INVENTOR(S)   : Kurokawa et al.

It is certified that error appears in the above-identified patent and that said Letters Patent is hereby corrected as shown below:

Column 2,
Line 49, "$\Phi = 20°$ serves" should read -- $\Phi = 2°$ serves --.

Column 4,
Line 59, "$\Phi \geqq 11°)$" should read -- $\Phi \geq 11°)$ --.

Signed and Sealed this

Thirteenth Day of July, 2004

JON W. DUDAS
*Acting Director of the United States Patent and Trademark Office*